United States Patent
Hu et al.

(10) Patent No.: US 12,151,046 B2
(45) Date of Patent: Nov. 26, 2024

(54) COMPOSITE ANTIBACTERIAL HYDROGEL DRESSING, PREPARATION METHOD AND APPLICATION THEREOF

(71) Applicant: Guangdong Ocean University, Zhanjiang (CN)

(72) Inventors: Zhang Hu, Zhanjiang (CN); Lefan Li, Zhanjiang (CN); Mingneng Liao, Zhanjiang (CN)

(73) Assignee: Guangdong Ocean University, Zhanjiang (CN)

( * ) Notice: Subject to any disclaimer, the term of this patent is extended or adjusted under 35 U.S.C. 154(b) by 0 days.

(21) Appl. No.: 18/648,498

(22) Filed: Apr. 29, 2024

(65) Prior Publication Data

US 2024/0277894 A1 Aug. 22, 2024

Related U.S. Application Data

(63) Continuation of application No. PCT/CN2023/128292, filed on Oct. 31, 2023.

(30) Foreign Application Priority Data

Dec. 29, 2022 (CN) .......................... 202211709193.9

(51) Int. Cl.
*A61L 26/00* (2006.01)
*C08L 5/08* (2006.01)

(52) U.S. Cl.
CPC ....... *A61L 26/0095* (2013.01); *A61L 26/0004* (2013.01); *A61L 26/0023* (2013.01); *A61L 26/0052* (2013.01); *A61L 26/0066* (2013.01); *A61L 26/008* (2013.01); *C08L 5/08* (2013.01); *A61L 2300/106* (2013.01); *A61L 2300/406* (2013.01)

(58) Field of Classification Search
None
See application file for complete search history.

(56) References Cited

U.S. PATENT DOCUMENTS

2002/0119205 A1* 8/2002 Hassan ................. A61K 47/61
514/55

OTHER PUBLICATIONS

Nakamura et al.(Controlled Synthesis of a Chitosan-Based Graft Copolymer Having Polysarcosine Side Chains Using the NCA Method with a Carboxylic Acid Additive. Macromol. Rapid Commun. 2006, 27, 1725-1732). (Year: 2006).*

* cited by examiner

*Primary Examiner* — Jake M Vu

(57) ABSTRACT

A composite antibacterial hydrogel dressing, a preparation method and an application method thereof are provided, which relate to the field of biomedical technologies. The composite antibacterial hydrogel dressing is made from the following raw materials in parts by weight: 8 to 22 parts of chitosan, 12 to 36 parts of carrageenan, 9 to 25 parts of 2-aminoisonicotinic acid, 3 to 8 parts of lactic acid, 4 to 10 parts of iodine and 6 to 15 parts of potassium iodide. The composite antibacterial hydrogel dressing has a good flexibility, a strong antibacterial effect, a long antibacterial time, no skin irritation, good application prospect in the field of medical wound repair, simple preparation process and easy industrial production.

7 Claims, 4 Drawing Sheets

COMPOSITE ANTIBACTERIAL HYDROGEL DRESSING, PREPARATION METHOD AND APPLICATION THEREOF

TECHNICAL FIELD

The disclosure relates to the field of biomedical technologies, and more particularly to a composite antibacterial hydrogel dressing, a preparation method and an application thereof.

BACKGROUND

A skin trauma caused by sharp tools, accidents, accidental burns, and major and minor surgeries is a serious problem, which directly relates to physical and mental health of an injured person. Differentiation of fibroblasts will be damaged when a wound infected by bacteria cannot heal quickly, which ultimately directly damage other normal tissues and immune systems in a body.

At present, a large number of studies have been developed to find a bioactive compound and polymer for preparing a wound dressing, so as to improve speed of wound healing and repair. A biomaterial with an intrinsic antibacterial active ingredient may have more advantages than a material containing a synthetic antibacterial drug due to existences of a large number of antibacterial resistance phenomena and inefficiency against non-targeted microorganism. Chitosan is one of few recommended hemostatic dressings for battlefield use. The chitosan has a broad-spectrum antibacterial activity, but has a poor antibacterial ability. Meanwhile, the chitosan is greatly affected by its parameters such as molecular weight, degree of deacetylation and potential of hydrogen (pH), and is limited in application. Therefore, how to improve an antibacterial effect of the chitosan while exerting a lasting antibacterial effect of the chitosan becomes an important development direction of a gel dressing of the chitosan.

SUMMARY

Aiming at the above problems in the related art, the disclosure provides a composite antibacterial hydrogel dressing, a preparation method and an application method thereof. A composite antibacterial hydrogel dressing with good physical and chemical properties and significant antibacterial effect is prepared by using chitosan, carrageenan, 2-aminoisonicotinic acid, lactic acid, iodine and potassium iodide as raw materials. The composite antibacterial hydrogel dressing integrates functions of good flexibility, strong antibacterial effect, moisture absorption and skin friendly, and no skin irritation, and has iodine slow release, thus exerting a long-term antibacterial effect, and the composite antibacterial hydrogel dressing also has characteristics of simple process and easy industrial production.

In order to achieve the above purposes, the disclosure provides a composite antibacterial hydrogel dressing, which is made from the following raw materials in parts by weight: 8 to 22 parts of chitosan, 12 to 36 parts of carrageenan, 9 to 25 parts of 2-aminoisonicotinic acid, 3 to 8 parts of lactic acid, 4 to 10 parts of iodine and 6 to 15 parts of potassium iodide.

In an embodiment, the composite antibacterial hydrogel dressing has a cross-linked network structure, and the cross-linked network structure includes multiple chitosan main chains and multiple carrageenan main chains. The chitosan main chains are connected to the carrageenan main chains through hydrogen bonding interactions and electrostatic interactions, the carrageenan main chains are connected to each other through hydrogen bonding interactions, and the chitosan main chains are connected to each other through π-π stacking interactions and hydrogen bonding interactions. The chitosan main chains are the chitosan-aminoisonicotinic acid-iodine complex, and the carrageenan main chains are the kappa carrageenan. After freeze-drying the composite antibacterial hydrogel dressing, the composite antibacterial hydrogel dressing becomes a solid and has a porous layered structure.

In an embodiment, the composite antibacterial hydrogel dressing is made from the following raw materials in parts by weight: 15 parts of the chitosan, 24 parts of the carrageenan, 17 parts of the 2-aminoisonicotinic acid, 5 parts of the lactic acid, 7 parts of the iodine and 10 parts of the potassium iodide.

Chitin, consisting of 2-acetamido-2-deoxy-beta-d-glucose through a beta (1→4) linkage, is a marine polysaccharide mainly derived from shells of marine organisms such as shrimp and crab, and a production of the chitin in nature is second only to the most abundant natural polymer cellulose. A deacetylation product of the chitin is chitosan, which is a natural cationic polysaccharide with good biological characteristics, such as biocompatibility, biodegradability, safety and non-toxicity. Meanwhile, the chitosan also has various functional characteristics, such as film forming, moisture retention, adsorption, hemostasis and healing promotion. In addition, as a main component of a skin care product, the chitosan has a broad-spectrum antibacterial ability, which plays a role of a natural antibiotic. However, the chitosan has a poor water-solubility and a week antibacterial activity, and an antibacterial activity of the chitosan is limited by various factors, such as a degree of deacetylation, a molecular weight and a concentration. The physical and chemical properties and the functional characteristics of the chitosan can be significantly improved through functional modification.

Beneficial effects of the disclosure are as follows. The carrageenan, extracted from several red seaweed species, is a hydrophilic sulfated polysaccharide made of alternating 3-linked β-D-galactopyranose and 4-linked α-D-galactopyranose or 4-linked 3,6-anhydro-α-D-galactopyranose. Natural carrageenan is divided into six types according to positions and numbers of sulfate groups in a molecular structure of the carrageenan, and the six types of the natural carrageenan are respectively kappa carrageenan (κ-carrageenan), iota carrageenan (ι-carrageenan), lambda carrageenan (λ-carrageenan), mu carrageenan (μ-carrageenan), nu carrageenan (ν-carrageenan) and theta carrageenan (θ-carrageenan). Carrageenan polysaccharides have a wide range of biological activities, such as anti-inflammatory, antioxidant and immunomodulatory.

In an embodiment, a degree of deacetylation of the chitosan is larger than or equal to 95%; and the carrageenan is the κ-carrageenan.

When the degree of deacetylation of the chitosan is too low, a number of free amino groups in a structure of the chitosan is decreased, positively charged quantity and capacity of loading the iodine are decreased, and an antibacterial effect of the prepared composite hydrogel dressing is poor.

The disclosure further provides a preparation method of the composite antibacterial hydrogel dressing, and the preparation method includes:

(1) adding an anhydrous ethanol solution of the 2-aminoisonicotinic acid and a coupling agent into a chitosan solution and stirring to obtain a first mixture, dialyzing the first mixture with distilled water to obtain a dialyzed mixture, and freeze-drying the dialyzed mixture to obtain a chitosan-aminoisonicotinic acid graft;

(2) adding the lactic acid, the iodine, the potassium iodide and water into the chitosan-aminoisonicotinic acid graft obtained in step (1) and stirring evenly to obtain a second mixture, and water-assisted grinding the second mixture to obtain a chitosan-aminoisonicotinic acid-iodine complex; and (3) adding the chitosan-aminoisonicotinic acid-iodine complex obtained in step (2) into a carrageenan solution and stirring to obtain a third mixture, performing a freeze-thaw cycle on the third mixture to obtain the composite antibacterial hydrogel dressing.

In an embodiment, a solvent of the chitosan solution in the step (1) is an acetic acid solution. A mass fraction of the chitosan in the chitosan solution is in a range of 1% to 5%. The coupling agent is 1-ethyl-3-(3-dimethylaminopropyl) carbodiimide hydrochloride (EDC·HCl) and N-hydroxy succinimide (NHS). A molar ratio of the 2-aminoisonicotinic acid:the EDC·HCl:the NHS is 3:6:2. A volume of the anhydrous ethanol solution is 15% to 25% of a volume of the chitosan solution. A time for stirring is in a range of 8 to 12 hours (h).

When the mass fraction of the chitosan in the chitosan solution is too low, difficultly of subsequent processes is improved, and a comprehensive performance of the prepared composite antibacterial hydrogel dressing is weakened. When the mass fraction of the chitosan in the chitosan solution is too high, a solution system of the chitosan solution is too viscous, which causing uneven reaction, and a poor antibacterial effect of the composite antibacterial hydrogel dressing.

When the volume of the anhydrous ethanol solution is too small, the concentration of 2-aminoisonicotinic acid and the coupling agent is too large, which causing an uneven reaction after adding the anhydrous ethanol solution of 2-aminoisonicotinic acid and the coupling agent into the chitosan solution, and a poor antibacterial effect of the composite material. When the volume of the anhydrous ethanol solution is too large, a direct precipitation of the chitosan is caused after adding the anhydrous ethanol solution of 2-aminoisonicotinic acid and the coupling agent into the chitosan solution, thus causing the prepared composite antibacterial hydrogel dressing without significant antibacterial effect.

In an embodiment, the volume of the anhydrous ethanol solution is 20% of the volume of the chitosan solution; and the mass fraction of the chitosan in the chitosan solution is 3%.

In an embodiment, a time for grinding in the step (2) is in a range of 0.4 to 0.6 h. The water-assisted grinding the second mixture refers to that a water mass content of the second mixture is in a range of 20% to 30% after adding the lactic acid, the iodine, the potassium iodide and water into the chitosan-aminoisonicotinic acid graft.

The lactic acid (2-hydroxy propionic acid) is a natural organic acid with a α-hydroxy acid structure, and the lactic acid can directly participate in a metabolic cycle, and is widely applied in food, pharmaceutical, chemical and other fields. On the one hand, lactic acid forms hydrogen bonds and electrostatic interactions with the hydroxyl and amino groups of chitosan, which enhances the encapsulation effect on iodine or triiodide ions ($I_3^-$), thereby enhancing the antibacterial effect of the composite antibacterial hydrogel dressing. On the other hand, due to a good water-holding capacity of the lactic acid, more water is kept in the composite antibacterial hydrogel dressing, and the hydrogen bonds are increased, which leads to an increase of flexibility of a polymer chain of the composite antibacterial hydrogel dressing, and an apparent performance is that an elasticity of the composite antibacterial hydrogel dressing is enhanced.

In an embodiment, a mass fraction of the carrageenan in the carrageenan solution in the step (3) is in a range of 1.0% to 3.5%. The number of the freeze-thaw cycles is in a range of 1 to 3 times.

During the freeze-thaw cycle, microcrystals are formed in the solution, and the nearby molecules are squeezed to form molecular aggregation areas, which makes the occurrence frequency of intermolecular and intramolecular hydrogen bonds increase, thus forming a uniform and stable composite antibacterial hydrogel dressing. However, a certain degree of water separation of a carrageenan gel is occurred during the freeze-thaw cycle, so that the number of the freeze-thaw cycles should not be too many.

In an embodiment, the mass fraction of the carrageenan in the carrageenan solution is 2.5%. The number of the freeze-thaw cycles is 2 times.

The disclosure further provides an application method of the composite antibacterial hydrogel dressing on a biochemical field, and the application method includes:

preparing a medical antibacterial and wound repair material by using the composite antibacterial hydrogel dressing; where the composite antibacterial hydrogel dressing has a good antibacterial activity against *Staphylococcus aureus* and *Escherichia coli*.

Compared to the related art, the beneficial effects of the disclosure are as follows.

The composite antibacterial hydrogel dressing prepared by the disclosure has a strong antibacterial effect and a long antibacterial time, and the composite antibacterial hydrogel dressing has a good application prospect in a preparation of the medical antibacterial and wound repair material.

In the disclosure, the 2-aminoisonicotinic acid is introduced onto the molecular chains of the chitosan through an amidation reaction using the coupling agent of the EDC·HCl and the NHS to form a chitosan-aminoisonicotinic acid graft. The amino groups of aminoisonicotinic acid residue in chitosan-aminoisonicotinic acid graft are protonated to form a stable conjugated structure of nitrogen-carbon-nitrogen $(N-C-N)^+$. On the one hand, the $(N-C-N)^+$ structure enhances an interaction with the negatively charged bacteria surfaces, and damages cell membrane of the bacteria to leak intracellular components, so as to exert an antibacterial effect. On the other hand, the $(N-C-N)^+$ residue of chitosan-aminoisonicotinic acid graft forms a stable six-membered ring complex with the triiodide ions through the electrostatic interaction, which can effectively solve the instability and non-persistence of the iodine, fully exert a synergistic antibacterial effect of the modified chitosan and the iodine, and significantly improve the antibacterial effect.

The disclosure utilizes characteristics of a natural seaweed polysaccharide carrageenan structure containing negatively charged sulfate groups and active hydroxyl groups, under a physical operation of the freeze-thaw cycle, a stable composite antibacterial hydrogel dressing is formed by the natural seaweed polysaccharide carrageenan and the 2-aminoisonicotinic acid modified chitosan through intramolecular and intermolecular hydrogen bonding and electrostatic interaction, without adding a chemical crosslinking agent.

In the disclosure, the lactic acid is added, on the one hand, a composite degree between the modified chitosan and the iodine is improved, and the antibacterial effect is improved; and on the other hand, the flexibility of the composite antibacterial hydrogel dressing is improved, and the elasticity of the composite antibacterial hydrogel dressing is enhanced.

The composite antibacterial hydrogel dressing prepared by the disclosure has a high biosafety, a simple preparation process, and is easy to industrialize production.

BRIEF DESCRIPTION OF DRAWINGS

In order to provide a clearer description of technical solutions in embodiments of the disclosure or related art, drawings required in the embodiments will be simply introduced below. Apparently, the drawings in the following descriptions are merely some of the embodiments, for those skilled in the art, other drawings can be obtained according to the drawings without creative work.

DETAILED DESCRIPTION OF EMBODIMENTS

Figure 1A:
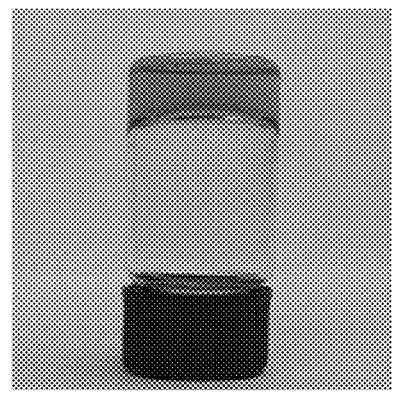
FIG. 1a illustrates a schematic diagram of an appearance of a composite antibacterial hydrogel dressing according to an embodiment 1 of the disclosure.

Embodiments of the disclosure are described in detail, and the detailed description should not be considered as a limitation of the disclosure, but should be understood as a more detailed description of certain aspects, characteristics and embodiments of the disclosure.

It should be understood that terms described in the disclosure are merely to describe specific embodiments, not to limit the disclosure. In addition, a numerical range in the disclosure should be understood as also specifically disclosing each intermediate value between an upper limit and a lower limit of the numerical range. Each smaller range between any stated value or intermediate value within the stated range, as well as any other stated value or intermediate value within the stated range, is also included in the disclosure. The upper and lower limits of the smaller ranges can be independently included or excluded from the range.

Unless otherwise specified, all technical and scientific terms used in this article have the same meanings as those commonly understood by those skilled in the art described herein. Although the disclosure merely describes some methods and materials, any methods and materials similar or equivalent to those described herein may also be used in the implementation or testing of the disclosure. All literature mentioned in the specification is incorporated by reference to publicly disclose and describe methods and/or materials related to the literature. In case of conflict with any incorporated literature, a content of the specification shall prevail.

It is obvious to those skilled in the art that many improvements and changes can be made to the embodiments of the disclosure without departing from a scope or spirit of the disclosure. Other embodiments obtained from the specification of the disclosure are obvious to those skilled in the art. The specification and embodiments of the disclosure are only illustrative.

Terms "comprising", "including", "having", "containing", and the like used in the article are all open-ended terms, meaning to include but not limited to.

Room temperature in the embodiments of the disclosure refers to a range of 23 Celsius degrees (° C.) to 27° C.

The embodiments of the disclosure provide a composite antibacterial hydrogel dressing, which is made from the following raw materials in parts by weight: 8 to 22 parts of chitosan, 12 to 36 parts of carrageenan, 9 to 25 parts of 2-aminoisonicotinic acid, 3 to 8 parts of lactic acid, 4 to 10 parts of iodine and 6 to 15 parts of potassium iodide.

In some embodiments of the disclosure, the composite antibacterial hydrogel dressing is made from the following raw materials in parts by weight: 15 parts of the chitosan, 24 parts of the carrageenan, 17 parts of the 2-aminoisonicotinic acid, 5 parts of the lactic acid, 7 parts of the iodine and 10 parts of the potassium iodide.

In some embodiments of the disclosure, a degree of deacetylation of the chitosan is larger than or equal to 95%; and the carrageenan is the κ-carrageenan.

The embodiments of the disclosure further provide a preparation method of the composite antibacterial hydrogel dressing, and the preparation method includes the following steps (1) to (3).

In step (1), an anhydrous ethanol solution of the 2-aminoisonicotinic acid and a coupling agent is added into a chitosan solution to obtain a first mixture after stirring. The first mixture is dialyzed with distilled water to obtain a dialyzed mixture. The dialyzed mixture is freeze-dried to obtain a chitosan-aminoisonicotinic acid graft.

In step (2), the lactic acid, the iodine, the potassium iodide and distilled water are added into the chitosan-aminoisonicotinic acid graft obtained in step (1) to obtain a second mixture after stirring evenly. The second mixture is water-assisted ground to obtain a chitosan-aminoisonicotinic acid-iodine complex.

In step (3), the chitosan-aminoisonicotinic acid-iodine complex obtained in step (2) is added into a carrageenan solution to obtain a third mixture after stirring. A freeze-thaw cycle is performed on the third mixture to obtain the composite antibacterial hydrogel dressing.

In some embodiments of the disclosure, a solvent of the chitosan solution in the step (1) is an acetic acid solution. A mass concentration of acetic acid in the acetic acid solution is in a range of 0.5% to 2%. A mass fraction of the chitosan in the chitosan solution is in a range of 1% to 5%. The coupling agent is EDC.HCl and NHS. A molar ratio of the 2-aminoisonicotinic acid:the EDC·HCl:the NHS is 3:6:2. A volume of the anhydrous ethanol solution is 15% to 25% of a volume of the chitosan solution. A time for stirring is in a range of 8 to 12 h.

In some embodiments of the disclosure, the volume of the anhydrous ethanol solution is 20% of the volume of the chitosan solution; and the mass fraction of the chitosan in the chitosan solution is 3%.

In some embodiments of the disclosure, a time for grinding in the step (2) is in a range of 0.4 to 0.6 h. A mass fraction of the carrageenan in the carrageenan solution in the step (3) is in a range of 1.0% to 3.5%. A number of the freeze-thaw cycles is in a range of 1 to 3 times.

In some embodiments of the disclosure, the mass fraction of the carrageenan in the carrageenan solution is 2.5%. The number of the freeze-thaw cycles is 2 times.

The embodiments of the disclosure further provides an application method of the composite antibacterial hydrogel dressing on a biochemical field, and the application method includes: preparing a medical antibacterial and wound repair material by using the composite antibacterial hydrogel dressing.

Embodiment 1

A preparation method of a composite antibacterial hydrogel dressing is provided, and the preparation method includes the following steps (1) to (6).

In step (1), 15 grams (g) of chitosan (a degree of deacetylation is larger than or equal to 95%) is added into 485 g (482 milliliters abbreviated as mL) of acetic acid solution (a mass concentration of acetic acid in the acetic acid solution is 1%) for stirring to dissolve, to thereby obtain a chitosan solution.

In step (2), 17 g (0.123 moles abbreviated as mol) of 2-aminoisonicotinic acid is dissolved in 96 mL of anhydrous ethanol solution, 0.246 mol of EDC·HCl and 0.082 mol of NHS are added into the anhydrous ethanol solution dissolved with the 2-aminoisonicotinic acid to stir at the room temperature for 5 h, to obtain an ethanol solution of the 2-aminoisonicotinic acid and the coupling agent (i.e., a mixture of EDC·HCl and NHS).

In step (3), the ethanol solution of the 2-aminoisonicotinic acid and the coupling agent prepared in the step (2) is added into the chitosan solution prepared in the step (1), followed by stirring them at the room temperature for 10 h to obtain a first mixture. The first mixture is dialyzed with distilled water to obtain a dialyzed mixture. The dialyzed mixture is freeze-dried to obtain a chitosan-aminoisonicotinic acid graft.

In step (4), 5 g of lactic acid, 7 g of iodine and 10 g of potassium iodide are added into the chitosan-aminoisonicotinic acid graft prepared in the step (3), distilled water is dropwise added into the chitosan-aminoisonicotinic acid graft added with the lactic acid, the iodine and the potassium iodide, followed by stirring them evenly to obtain a second mixture. The second mixture is water-assisted ground for 0.5 h to obtain a chitosan-aminoisonicotinic acid-iodine complex.

In step (5), 24 g of κ-carrageenan is added into 936 g of distilled water for stirring and dissolving in a water bath at 60° C. to obtain a κ-carrageenan solution (a mass fraction is 2.5%).

Figure 5:
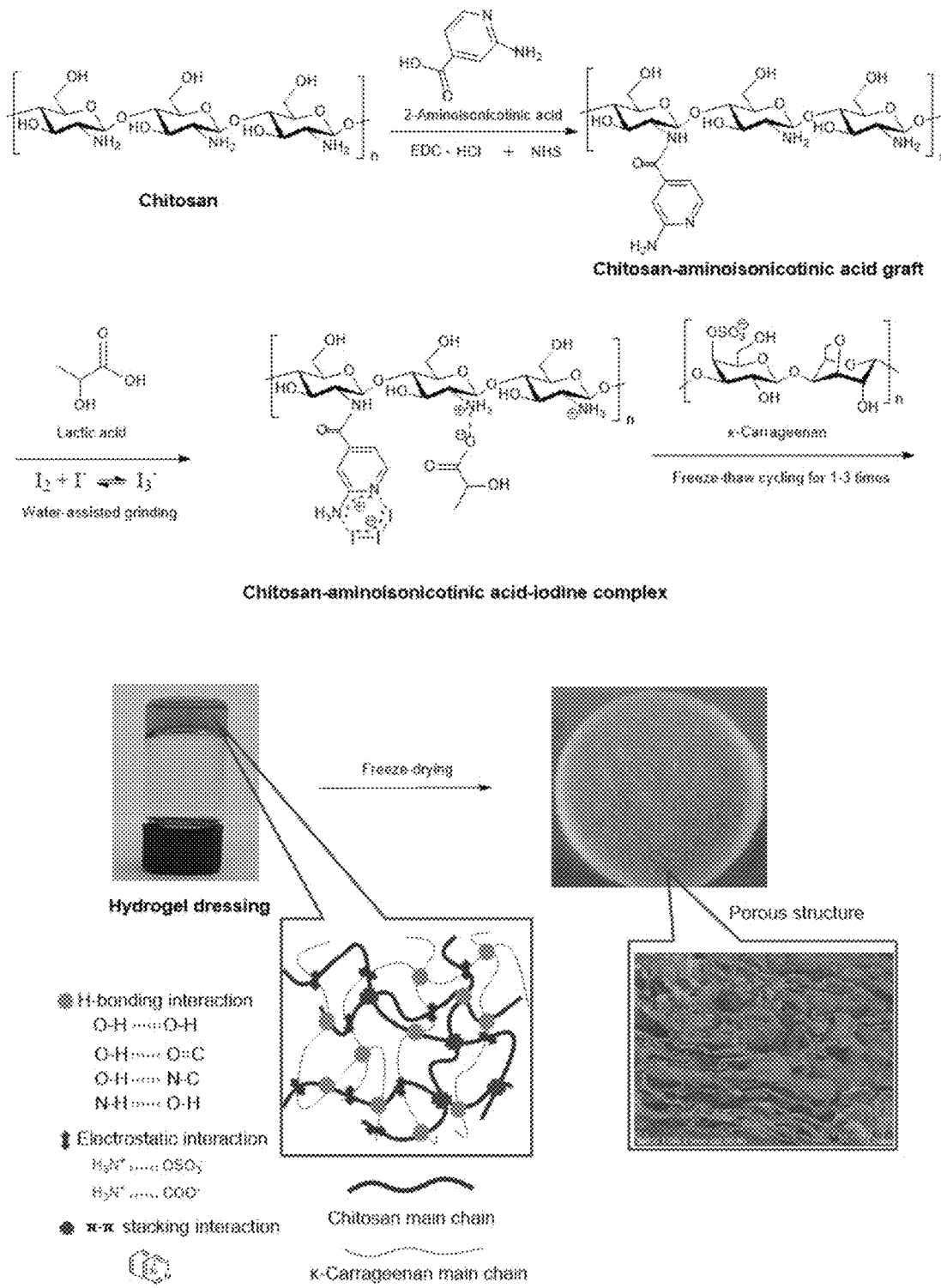
FIG. 5 illustrates a schematic diagram of a specific synthesis process of the composite antibacterial hydrogel dressing according to embodiments of the disclosure.

In step (6), the chitosan-aminoisonicotinic acid-iodine complex prepared in the step (4) is added into the κ-carrageenan solution prepared in the step (5), followed by stirring them evenly in the water bath at 60° C. to obtain a third mixture. The third mixture is poured into a mold and allowed to stand at the room temperature to form a gel. The gel is transferred to a temperature of −20° C. and frozen for 24 h, and then thawed at the room temperature for 5 h, this freeze-thaw cycle (i.e., the gel is frozen at −20° C. for 24 h and then thawed at the room temperature for 5 h) is performed on the gel for twice, to thereby obtain the composite antibacterial hydrogel dressing (refer to FIG. 5).

Figure 1B:
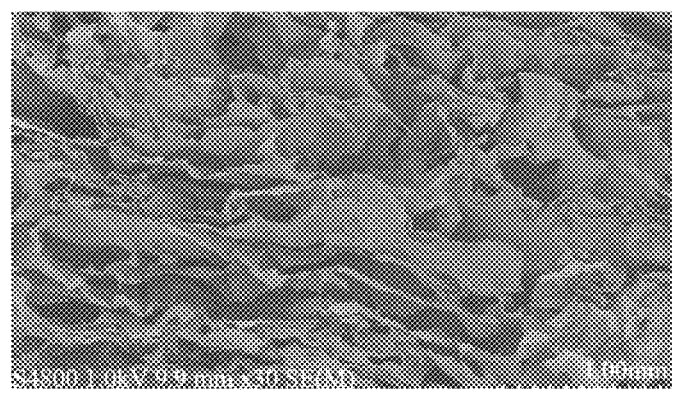
FIG. 1b illustrates a scanning electron microscope diagram of a freeze-dried sample surface of the composite antibacterial hydrogel dressing according to the embodiment 1 of the disclosure.

FIG. 1a illustrates a schematic diagram of an appearance of the composite antibacterial hydrogel dressing prepared in the embodiment 1, and FIG. 1b illustrates a scanning electron microscope diagram of a freeze-dried sample surface of the composite antibacterial hydrogel dressing prepared in the embodiment 1.

It can be seen from FIG. 1a that the composite antibacterial hydrogel dressing is light yellowish brown, translucent, and adheres to a bottom of the bottle, and upside down without falling off. After the composite antibacterial hydrogel dressing is freeze-dried to obtain a dried composite antibacterial hydrogel dressing, the scanning electron microscope diagram of the dried composite antibacterial hydrogel dressing is shown in FIG. 1b, the dried composite antibacterial hydrogel dressing has a porous layered structure, good permeability and large absorption capacity for liquid, which provides a moist microenvironment for skin cells and is beneficial to wound repair.

Embodiment 2

A preparation method of a composite antibacterial hydrogel dressing is provided, and the preparation method includes the following steps (1) to (6).

In step (1), 8 g of chitosan (a degree of deacetylation is larger than or equal to 95%) is added into 792 g (786 mL) of acetic acid solution (a mass concentration of acetic acid in the acetic acid solution is 0.5%) for stirring to dissolve, to thereby obtain a chitosan solution.

In step (2), 9 g (0.065 mol) of 2-aminoisonicotinic acid is dissolved in 118 mL of anhydrous ethanol solution, 0.13 mol of EDC·HCl and 0.043 mol of NHS are added into the anhydrous ethanol solution dissolved with the 2-aminoisonicotinic acid to stir at the room temperature for 5 h, to obtain an ethanol solution of the 2-aminoisonicotinic acid and the coupling agent.

In step (3), the ethanol solution of the 2-aminoisonicotinic acid and the coupling agent prepared in the step (2) is added into the chitosan solution prepared in the step (1), followed by stirring them at the room temperature for 8 h to obtain a first mixture. The first mixture is dialyzed with distilled water to obtain a dialyzed mixture. The dialyzed mixture is freeze-dried to obtain a chitosan-aminoisonicotinic acid graft.

In step (4), 3 g of lactic acid, 4 g of iodine and 6 g of potassium iodide are added into the chitosan-aminoisonicotinic acid graft prepared in the step (3), distilled water is dropwise added into the chitosan-aminoisonicotinic acid graft added with the lactic acid, the iodine and the potassium iodide, followed by stirring them evenly to obtain a second mixture. The second mixture is water-assisted ground for 0.4 h to obtain a chitosan-aminoisonicotinic acid-iodine complex.

In step (5), 12 g of κ-carrageenan is added into 1188 g of distilled water for stirring and dissolving in a water bath at 60° C. to obtain a κ-carrageenan solution (a mass fraction is 1.0%).

In step (6), the chitosan-aminoisonicotinic acid-iodine complex prepared in the step (4) is added into the κ-carrageenan solution prepared in the step (5), followed by stirring them evenly in the water bath at 60° C. to obtain a third mixture. The third mixture is poured into the mold and allowed to stand at the room temperature to form a gel. The gel is transferred to a temperature of −20° C. and frozen for 24 h, and then thawed at the room temperature for 5 h, to thereby obtain the composite antibacterial hydrogel dressing (refer to FIG. 5).

Embodiment 3

A preparation method of a composite antibacterial hydrogel dressing is provided, and the preparation method includes the following steps (1) to (6).

In step (1), 22 g of chitosan (a degree of deacetylation is larger than or equal to 95%) is added into 418 g (415 mL) of acetic acid solution (a mass concentration of acetic acid in the acetic acid solution is 2%) for stirring to dissolve, to thereby obtain a chitosan solution.

In step (2), 25 g (0.181 mol) of 2-aminoisonicotinic acid is dissolved in 104 mL of anhydrous ethanol solution, 0.362 mol of EDC·HCl and 0.121 mol of NHS are added into the anhydrous ethanol solution dissolved with the 2-aminoisonicotinic acid to stir at the room temperature for 5 h, to obtain an ethanol solution of the 2-aminoisonicotinic acid and the coupling agent.

In step (3), the ethanol solution of the 2-aminoisonicotinic acid and the coupling agent prepared in the step (2) is added into the chitosan solution prepared in the step (1), followed by stirring them at the room temperature for 10 h to obtain a first mixture. The first mixture is dialyzed with distilled water to obtain a dialyzed mixture. The dialyzed mixture is freeze-dried to obtain a chitosan-aminoisonicotinic acid graft.

In step (4), 8 g of lactic acid, 10 g of iodine and 15 g of potassium iodide are added into the chitosan-aminoisonicotinic acid graft prepared in the step (3), distilled water is dropwise added into the chitosan-aminoisonicotinic acid graft added with the lactic acid, the iodine and the potassium iodide, followed by stirring them evenly to obtain a second mixture. The second mixture is water-assisted ground for 0.6 h to obtain a chitosan-aminoisonicotinic acid-iodine complex.

In step (5), 36 g of κ-carrageenan is added into 992 g of distilled water for stirring and dissolving in a water bath at 60° C. to obtain a κ-carrageenan solution (a mass fraction is 3.5%).

In step (6), the chitosan-aminoisonicotinic acid-iodine complex prepared in the step (4) is added into the κ-carrageenan solution prepared in the step (5), followed by stirring them evenly in the water bath at 60° C. to obtain a third mixture. The third mixture is poured into the mold and allowed to stand at the room temperature to form a gel. The gel is transferred to a temperature of −20° C. and frozen for 24 h, and then thawed at the room temperature for 5 h, the freeze-thaw cycle is performed on the gel for three times, to thereby obtain the composite antibacterial hydrogel dressing (refer to FIG. 5).

Comparative Embodiment 1

A preparation method of a composite antibacterial hydrogel dressing is provided, and a difference between the embodiment 1 and the comparative embodiment 1 is to replace the κ-carrageenan in the step (5) and the step (6) with sodium alginate.

Comparative Embodiment 2

A preparation method of a composite antibacterial hydrogel dressing is provided, and a difference between the embodiment 1 and the comparative embodiment 2 is to replace the 2-aminoisonicotinic acid in the step (2) with 3-aminobenzoic acid.

Comparative Embodiment 3

A preparation method of a composite antibacterial hydrogel dressing is provided, and a difference between the embodiment 1 and the comparative embodiment 3 is that the lactic acid is not added in the step (4).

Comparative Embodiment 4

A preparation method of a composite antibacterial hydrogel dressing is provided, and a difference between the embodiment 1 and the comparative embodiment 4 is to replace the water-assisted grinding method in the step (4) with a solution method, and an operation of the step (4) is as follows: the chitosan-aminoisonicotinic acid graft prepared in the step (3) is added into distilled water (a mass fraction is 3%), 5 g of lactic acid, 7 g of iodine and 10 g of potassium iodide are added into the distilled water added with the chitosan-aminoisonicotinic acid graft to stir for 0.5 h to obtain a mixture, and the mixture is freeze-dried to obtain a chitosan-aminoisonicotinic acid-iodine complex.

Effect Embodiment 1

A mechanical performance test of a tensile mode is performed on the composite antibacterial hydrogel dressings prepared in the embodiments 1 to 3 and the comparative embodiments 1 to 4, and a process of the mechanical performance test is as follows.

Each sample of the composite antibacterial hydrogel dressings prepared in the embodiments 1 to 3 and the comparative embodiments 1 to 4 is cut into a cuboid shape with a length of 40 millimeters (mm), a width of 5 mm and a thickness of 3 mm. A universal testing machine (INSTRON5982, USA) is used to determine a tensile strength ($\sigma$) and an elongation at break ($\varepsilon$) of each sample. The sample is stretched at a constant strain rate of 1 millimeter per minute (mm/min) until complete tensile failure occurs, and the test is repeated for four times, average values of the tensile strength and the elongation at break are taken, and test results are shown in Table 1.

TABLE 1

| Tensile mechanical properties of samples | | |
|---|---|---|
| Sample | Tensile strength ($\sigma$, megapascal abbreviated as MPa) | Elongation at break ($\varepsilon$, %) |
| Embodiment 1 | 8.63 ± 0.21 | 118 ± 4 |
| Embodiment 2 | 8.13 ± 0.17 | 115 ± 2 |
| Embodiment 3 | 8.46 ± 0.15 | 111 ± 5 |
| Comparative embodiment 1 | 5.86 ± 0.11 | 84 ± 3 |
| Comparative embodiment 2 | 6.95 ± 0.24 | 92 ± 7 |
| Comparative embodiment 3 | 6.04 ± 0.13 | 67 ± 6 |
| Comparative embodiment 4 | 7.32 ± 0.17 | 98 ± 3 |

The tensile strength reflects a mechanical strength of a material, and the larger the value of the tensile strength, the less likely the material is to be pulled apart. The elongation at break reflects a plasticity degree of the material, and the larger the value of the elongation at break, the better flexibility and elasticity of the material. As shown in Table 1, since the composite antibacterial hydrogel dressings of the embodiments 1 to 3 have a cross-linked network structure formed by multiple physical actions, the composite antibacterial hydrogel dressings have good elasticity and mechanical stability. Since starting materials of the composite antibacterial hydrogel dressings of the comparaembodiments 1 to 4 are replaced or omitted, or a preparation process of the composite antibacterial hydrogel dressings is changed, the tensile strength and the elongation at break of the composite antibacterial hydrogel dressings are significantly decreased, and the mechanical properties deteriorate.

Effect Embodiment 2

An iodine release performance test is performed on the composite antibacterial hydrogel dressing prepared in the embodiment 1, and a process of the iodine release performance test is as follows.

An iodometric method is used to determine an iodine content of the composite antibacterial hydrogel dressing (dry basis) prepared in the embodiment 1, and the iodine content is 8.23%. A standard curve method is used to determine an iodine release behavior in the composite antibacterial hydrogel dressing, and a specific process is as follows: phosphate buffer solutions of iodine (pH=7.4) with concentrations of $0.98 \times 10^{-4}$ moles per liter (mol/L), $1.97 \times 10^{-4}$ mol/L, $2.96 \times 10^{-4}$ mol/L, $3.94 \times 10^{-4}$ mol/L and $7.88 \times 10^{-4}$ mol/L are respectively prepared, an absorbance of each phosphate buffer solution of iodine at 226 nanometers (nm) is determined by using a ultraviolet spectrograph, and a linear fitting is performed on a concentration of iodine in the phosphate buffer solutions of iodine and the absorbance, a regression equation is expressed as $C=(13.63 A-0.58) \times 10^{-4}$ mol/L, and a correlation coefficient is 0.9997. Specifically, C represents the concentration of iodine in the phosphate buffer solution of iodine, and A represents an absorbance of the iodine at 226 nm. The sample is added into 500 mL of the phosphate buffer solution of iodine (pH=7.4) to be protected from light, and is shaken at a constant temperature of 37° C. to obtain a mixture. 2 mL of supernatant of the mixture is taken out every 5 minutes (min), and 2 mL of the phosphate buffer solution of iodine is added into the mixture to keep a total volume of the mixture unchanged. An absorbance of the supernatant at 226 nm is measured, and a standard linear regression equation is introduced to calculate a concentration of the supernatant at each moment.

Figure 2:
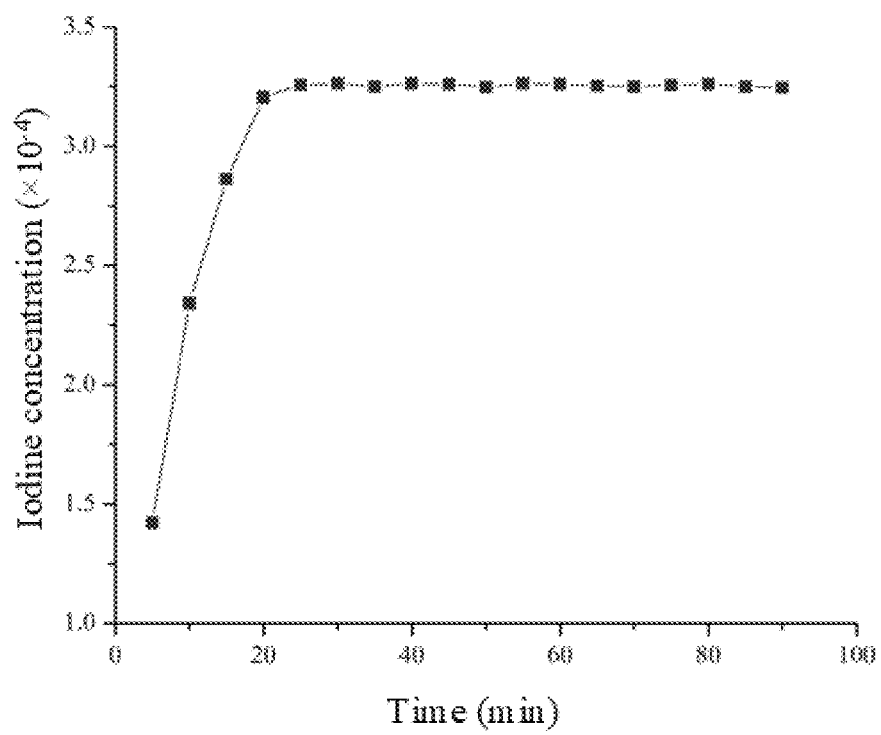
FIG. 2 illustrates a curve diagram of iodine release in vitro of the composite antibacterial hydrogel dressing according to the embodiment 1 of the disclosure.

An iodine release dynamic curve of the composite antibacterial hydrogel dressing prepared in the embodiment 1 is shown in FIG. 2. The iodine release process has a burst release period (0-15 min) and a rapid release period (15-25 min), after the concentration of iodine in the solution reaches $3.26 \times 10^{-4}$ mol/L, the iodine is in a slow release period. The iodine release of the composite antibacterial hydrogel dressing is suddenly released from surface of the composite antibacterial hydrogel dressing, and then spreads from the inside out, which indicates that the composite antibacterial hydrogel dressing has a slow release effect, high concentration aggregation is avoided, and irritation to traumatic skin is reduced. The burst release and the rapid release can rapidly achieve an effective concentration, and generate antibacterial property. After 2 days, the concentration of the iodine in the solution is detected, which reaches $3.05 \times 10^{-4}$ mol/L, and indicates that the iodine release and iodine loss are in a relative dynamic equilibrium state, and the slow release is beneficial for exerting a long-lasting antibacterial effect.

Effect Embodiment 3

An antibacterial performance test is performed on the composite antibacterial hydrogel dressings prepared in the embodiments 1 to 3 and the comparative embodiment 1 to 4, and a process of the antibacterial performance test is as follows.

A minimal inhibitory concentration (MIC) of each sample is determined by using a double dilution method. The composite antibacterial hydrogel dressing samples are dissolved in the acetic acid solution with a concentration of 2%, and a series of concentrations among 1024-0.5 microns per milliliter (μg/mL) are prepared through the double dilution method. Gram-positive Staphylococcus aureus (S. aureus, ATCC 6538) and gram-negative Escherichia coli (E. coli, ATCC 8739) are used as experimental bacteria, bacterial suspension without any sample treatment is used as a control group, and then they are incubated at 37° C. for 24 h to determine the MIC value.

The MIC is an indicator reflecting antibacterial activity of antibacterial substances, and the smaller the value, the stronger the antibacterial ability; and the larger the value, the weaker the antibacterial activity. Results of the MIC of the tested composite antibacterial hydrogel dressings are shown in Table 2. The MIC values of the embodiments 1 to 3 are relatively low, which indicates that the composite antibacterial hydrogel dressings have good antibacterial property. Since the starting materials of the composite antibacterial hydrogel dressings of the comparative embodiments 1 to 4 are replaced or omitted, or a preparation process of the composite antibacterial hydrogel dressings is changed, the antibacterial performance of the composite antibacterial hydrogel dressings of the comparative embodiments 1 to 4 is poor.

TABLE 2

MIC of the composite antibacterial hydrogel dressing samples

| Sample | MIC (μg/mL) | |
| --- | --- | --- |
| | S. aureus | E. coli |
| Embodiment 1 | 8 | 16 |
| Embodiment 2 | 8 | 32 |
| Embodiment 3 | 16 | 32 |
| Comparative embodiment 1 | 128 | 128 |
| Comparative embodiment 2 | 256 | 256 |
| Comparative embodiment 3 | 128 | 256 |
| Comparative embodiment 4 | 64 | 128 |

The raw material chitosan (the degree of deacetylation is larger than or equal to 95%), the chitosan-aminoisonicotinic acid graft prepared in the embodiment 1 and the composite antibacterial hydrogel dressing prepared in the embodiment 1 are used as testing samples. Inhibition zones of the testing samples for the S. aureus and the E. coli are determined by using an agar diffusion method, to thereby evaluate antibacterial performance of the testing samples.

1 mL of inoculation suspension with a concentration range of 106 to 107 colony-forming units per milliliter (CFU/mL) is sucked and mixed evenly with 10 mL of agar medium to obtain a mixture, and then the mixture is slowly poured into a sterile culture dish and allowed to stand and solidify. Sterilized oxford cups are gently stuck onto a surface of an agar plate (i.e., the sterile culture dish with the mixture) by using a sterile forceps, 100 microliters (μL) of the testing samples (100 μg/mL) are added dropwise into different oxford cups, and then the culture dish is incubated at 37° C. for 24 h. A digital camera is used to take photos for the inhibition zones and an ImageJ software is used to measure sizes of the inhibition zones, measure it in parallel for three times, and take its average value.

Figure 3:
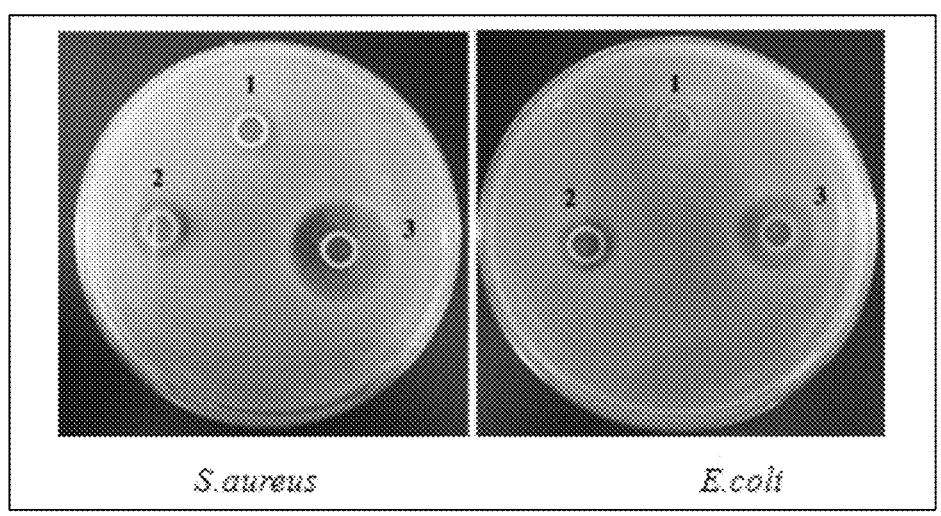
FIG. 3 illustrates a schematic diagram of experimental results of inhibition zones. Specifically, 1 represents an inhibition zone of chitosan (a degree of deacetylation is larger than or equal to 95%); 2 represents an inhibition zone of a chitosan-aminoisonicotinic acid graft in the embodiment 1; and 3 represents an inhibition zone of a sample of the composite antibacterial hydrogel dressing prepared in the embodiment 1.

Test results are shown in FIG. 3, an inhibition zone 1 represents an inhibition zone obtained by the raw material chitosan (the degree of deacetylation is larger than or equal to 95%), an inhibition zone 2 represents an inhibition zone obtained by the chitosan-aminoisonicotinic acid graft, and an inhibition zone 3 represents an inhibition zone obtained by the composite antibacterial hydrogel dressing prepared in the embodiment 1.

The test results indicate that the raw material chitosan (the degree of deacetylation is larger than or equal to 95%) has a certain inhibition effect on the tested bacteria, but the antibacterial effect is limited. Compared to the raw material chitosan, the chitosan-aminoisonicotinic acid graft has an increased antibacterial effect for the two tested bacteria, which indicates that the 2-aminoisonicotinic acid modifies the chitosan to improve the antibacterial effect of the chitosan. The inhibition zones of the composite antibacterial hydrogel dressing prepared in the embodiment 1 for the tested *S. aureus* and the *E. coli* respectively reaches 25.3±0.5 mm (i.e., 24.8-25.8 mm) and 18.7±0.3 mm (i.e., 18.4-19.0 mm), which have significant differences compared to the chitosan-aminoisonicotinic acid graft, and indicates that the composite antibacterial hydrogel dressing made of a polymer matrix material and iodine has synergistically enhanced antibacterial effect.

Effect Embodiment 4

The composite antibacterial hydrogel dressing prepared in the embodiment 1 is used as a testing sample to perform a skin irritation test, and a process of the skin irritation test is as follows.

The skin irritation test is performed according to a GB/T 16886.10-2017 biological evaluation standards for medical devices.

Figure 4:
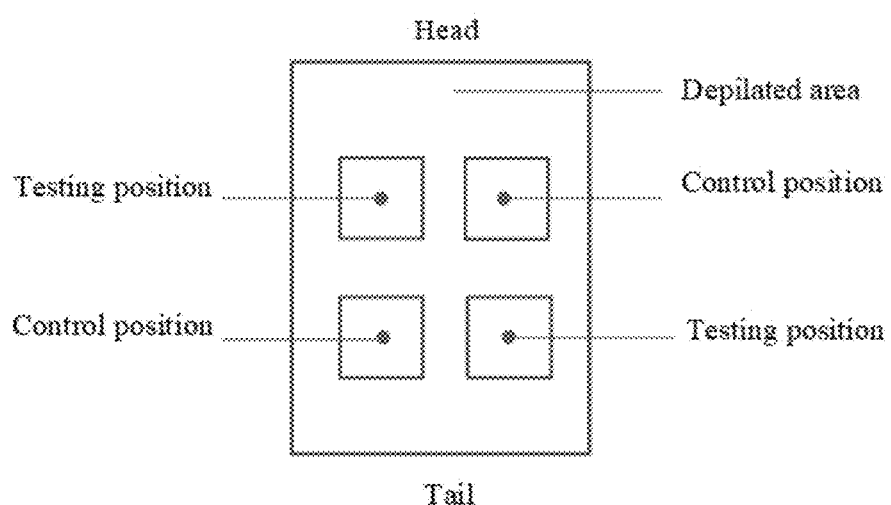
FIG. 4 illustrates a schematic diagram of a skin irritation test of the composite antibacterial hydrogel dressing according to the embodiment 1 of the disclosure.

3 healthy New Zealand white rabbits (2.1±0.1 kilograms abbreviated as kg) (regardless of gender) are adaptively raised for 1 week. Hairs on two sides of a back spine of each of the rabbits are cut off with an area of approximately 10 cm×15 cm by using scissors, and it necessary to ensure no damage to the skin. On the next day, two pieces of the composite antibacterial hydrogel dressing (sizes are approximately 2.5 cm×2.5 cm) prepared in the embodiment 1 are directly attached on the depilated skin on the two sides of the back of each of the rabbits (as shown in FIG. 4), contact positions are covered by using sterile gauzes, and the sterile gauzes are fixed on the contact positions with adhesive tape. In addition, in the depilated skin without hydrogel treatment, it is also covered with the sterile gauzes and the sterile gauzes are fixed with the adhesive tape as a blank control. After 6 h of application, the coverings (i.e., the sterile gauzes and the adhesive tape) on the skin are removed and residue on the skin surface is wiped with warm physiological saline. Local reactions of the treated skin are observed after 1 h, 24 h, 48 h and 72 h, and scoring is performed according to presence of erythema (0 points for no erythema, 1 point for barely visible erythema, 2 points for clear erythema, 3 points for moderate erythema, 4 points for severe purplish red erythema) and edema (0 points for no edema, 1 point for barely visible edema, 2 points for clear swelling margin, 3 points for swelling elevation of about 1 mm, 4 points for swelling elevation of more than 1 mm).

Skin irritation test results show that there is neither erythema nor edema on the rabbit skin surfaces, and a primary irritation score of the rabbit skin is 0, which indicates that the composite antibacterial hydrogel dressing prepared in the embodiment 1 has no irritation to the rabbit skin.

The embodiments described above are merely descriptions of implementation methods of the disclosure, and are not intended to limit the scope of the disclosure. Without departing from a design spirit of the disclosure, various modifications and improvements made by those skilled in the art to the technical solutions of the disclosure should fall within a scope of protection defined in claims of the disclosure.

What is claimed is:

1. A composite antibacterial hydrogel dressing, made from the following raw materials in parts by weight: 8 to 22 parts of chitosan, 12 to 36 parts of carrageenan, 9 to 25 parts of 2-aminoisonicotinic acid, 3 to 8 parts of lactic acid, 4 to 10 parts of iodine and 6 to 15 parts of potassium iodide; and
   wherein a preparation method of the composite antibacterial hydrogel dressing comprises:
   (1) adding an anhydrous ethanol solution of the 2-aminoisonicotinic acid and a coupling agent into a chitosan solution and stirring to obtain a first mixture, dialyzing the first mixture with distilled water to obtain a dialyzed mixture, and freeze-drying the dialyzed mixture to obtain a chitosan-aminoisonicotinic acid graft;
   (2) adding the lactic acid, the iodine, the potassium iodide and water into the chitosan-aminoisonicotinic acid graft obtained in step (1) and stirring evenly to obtain a second mixture, and water-assisted grinding the second mixture to obtain a chitosan-aminoisonicotinic acid-iodine complex; and
   (3) adding the chitosan-aminoisonicotinic acid-iodine complex obtained in step (2) into a carrageenan solution and stirring to obtain a third mixture, performing a freeze-thaw cycle on the third mixture to obtain the composite antibacterial hydrogel dressing.

2. The composite antibacterial hydrogel dressing as claimed in claim 1, comprising the following raw materials in parts by weight: 15 parts of the chitosan, 24 parts of the carrageenan, 17 parts of the 2-aminoisonicotinic acid, 5 parts of the lactic acid, 7 parts of the iodine and 10 parts of the potassium iodide.

3. The composite antibacterial hydrogel dressing as claimed in claim 1, wherein a degree of deacetylation of the chitosan is larger than or equal to 95%.

4. The composite antibacterial hydrogel dressing as claimed in claim 1, wherein the carrageenan is kappa-carrageenan (κ-carrageenan).

5. The composite antibacterial hydrogel dressing as claimed in claim 1, wherein a solvent of the chitosan solution in the step (1) is an acetic acid solution, and a mass fraction of the chitosan in the chitosan solution is in a range of 1% to 5%;
   the coupling agent is 1-ethyl-3-(3-dimethylaminopropyl) carbodiimide hydrochlorid (EDC·HCl) and N-hydroxy succinimide (NHS);
   a molar ratio of the 2-aminoisonicotinic acid:the 1-ethyl-3-(3-dimethylaminopropyl) carbodiimide hydrochloride:the N-hydroxy succinimide is 3:6:2; and
   a volume of the anhydrous ethanol solution is 15% to 25% of a volume of the chitosan solution.

6. The composite antibacterial hydrogel dressing as claimed in claim 1, wherein a time for the grinding in the step (2) is in a range of 0.4 to 0.6 hours (h).

7. The composite antibacterial hydrogel dressing as claimed in claim 1, wherein a mass fraction of the carrageenan in the carrageenan solution in the step (3) is in a range of 1.0% to 3.5%; and a number of the freeze-thaw cycle is in a range of 1 to 3 times.

* * * * *